United States Patent [19]
Shih

[11] Patent Number: 5,129,996
[45] Date of Patent: Jul. 14, 1992

[54] LOWER ALKYLENE OXIDE PURIFICATION

[75] Inventor: T. Thomas Shih, Bryn Mawr, Pa.

[73] Assignee: Arco Chemical Technology, L.P., Wilmington, Del.

[21] Appl. No.: 681,794

[22] Filed: Apr. 8, 1991

Related U.S. Application Data

[63] Continuation-in-part of Ser. No. 491,874, Mar. 12, 1990, abandoned.

[51] Int. Cl.⁵ .............................................. B01D 3/40
[52] U.S. Cl. ....................................... 203/64; 203/68; 549/541; 549/542
[58] Field of Search ........................... 203/63, 64, 68; 549/541, 542

[56] References Cited

U.S. PATENT DOCUMENTS

| | | | |
|---|---|---|---|
| 3,578,568 | 5/1971 | Washall | 203/64 |
| 3,838,020 | 9/1974 | Kageyama et al. | 203/64 |
| 3,909,366 | 9/1975 | Schmidt et al. | 203/69 |
| 4,402,794 | 9/1983 | Nemet-Mauradin et al. | 203/14 |

*Primary Examiner*—Virginia Manoharan
*Attorney, Agent, or Firm*—William C. Long

[57] ABSTRACT

A method is provided for the separation by extractive distillation of hydrocarbon impurities from lower alkylene oxides such as propylene oxide wherein a glycol having 2 to 5 carbon atoms is used as extractive solvent.

4 Claims, 1 Drawing Sheet

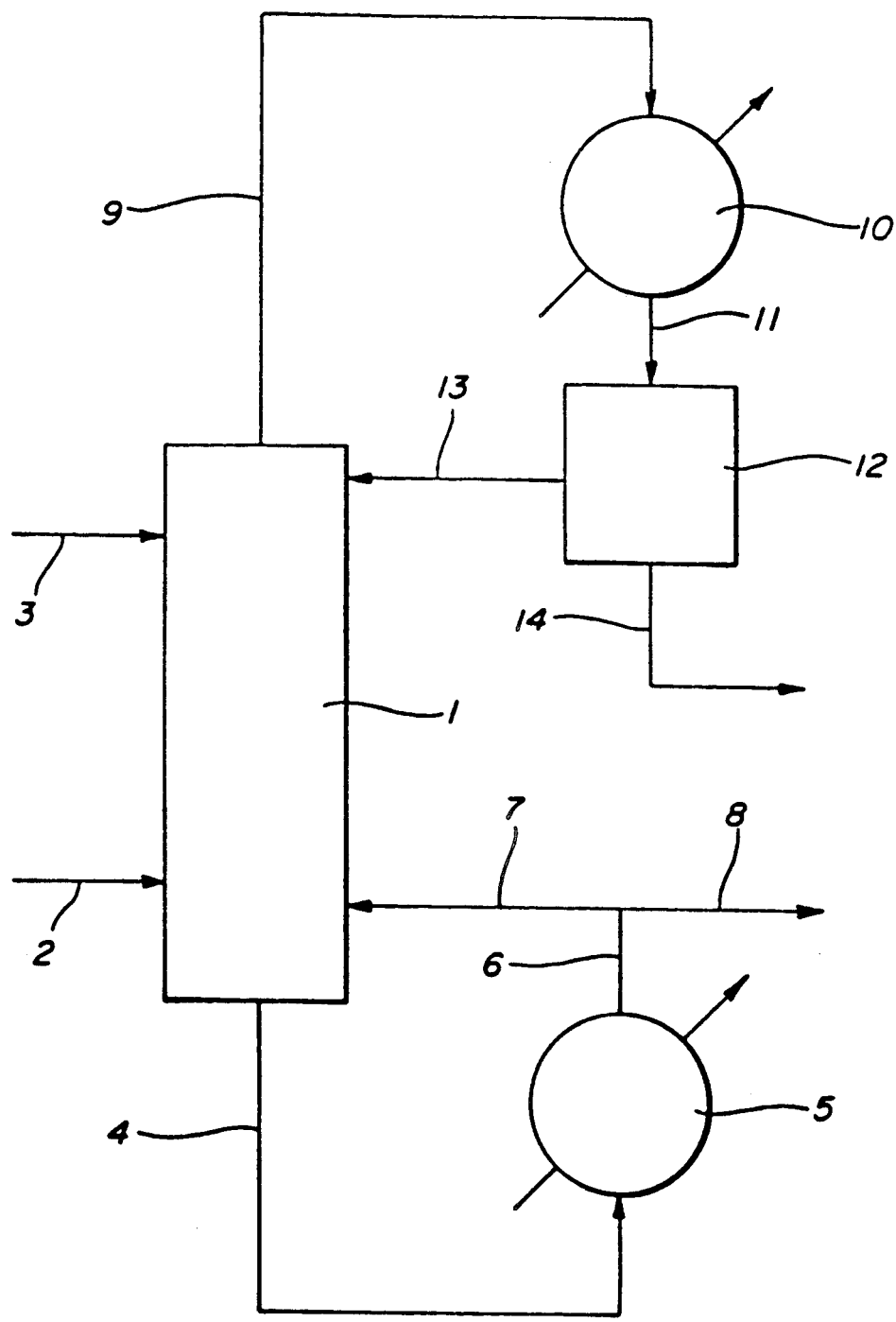

LOWER ALKYLENE OXIDE PURIFICATION

RELATED APPLICATION

This application is a continuation-in-part of co-pending application Ser. No. 07/491,074 filed March 12, 1990 now abandoned.

BACKGROUND OF THE INVENTION

1. Field of the Invention

The present invention relates to the separation of hydrocarbon impurities from lower alkylene oxides such as propylene oxide by extractive distillation with a glycol extractive solvent.

2. Description of the Prior Art

Monoepoxides such as propylene oxide are highly important chemicals useful in a great number of applications. An important commercial technology for producing the monoepoxides is via the catalytic reaction between the corresponding olefin and an organic hydroperoxide. See, for example, U.S. Pat. No. 3,351,635.

In carrying out this reaction the organic hydroperoxide is reduced to the corresponding alcohol. Also produced, however, are small amounts of other oxygen-containing compounds such as methanol, acetone, acetaldehyde and the like, as well as hydrocarbons which are difficult to separate. In general, the alcohol resulting from the reduction of the hydroperoxide can be separated from the epoxide product by ordinary distillation methods, particularly since the organic hydroperoxide employed can be selected to permit this separation. The small amounts of hydrocarbons and other oxygenated compounds, however, remain as impurities in the olefin oxide product. For certain of the epoxides, it is extremely important that these impurities be reduced to a very low ppm level, e.g., below about 200 ppm and especially below 50 ppm.

Hydrocarbon impurities associated with the lower alkylene oxides are paraffinic and olefinic hydrocarbons having 4 to 8 carbon atoms and in the case of propylene oxide are believed to be propylene derivatives having from 4 to 7 carbon atoms per molecule, primarily derivatives having 6 carbon atoms per molecule. The $C_6$ compounds include primarily methyl pentenes and methyl pentanes. These materials have boiling points sufficiently close to that of propylene oxide (about 35° C. at 760 mm/Hg) so that they are not effectively separated from propylene oxide by direct fractionation. In some cases an azeotrope is formed, making separation even more difficult.

U.S. Pat. No. 3,843,488 describes the separation of contaminating hydrocarbons from propylene oxide by distillation in the presence of a $C_8$ to $C_{20}$ alkane, alkene or naphthene. U.S. Pat. No. 3,909,366 describes the separation of contaminating hydrocarbons from propylene oxide by distillation in the presence of aromatic hydrocarbons having 6 to 12 carbon atoms. U.S. Pat. No. 3,464,897 shows propylene oxide purification by extractive distillation with aliphatic or cyclic paraffins having 8 to 12 carbon atoms.

It has previously been proposed to separate oxygen-containing impurities from the propylene oxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. U.S. Pat. No. 5,000,825 describes a similar separation but using much less solvent whereby propylene oxide losses are reduced.

BRIEF DESCRIPTION OF THE INVENTION

In accordance with the present invention, it has been found that lower alkylene oxides having 2 to 4 carbon atoms, particularly propylene oxide, containing hydrocarbon impurities having 4 to 8 carbon atoms can be purified by extractive distillation using glycols as extractive solvents.

BRIEF DESCRIPTION OF THE DRAWINGS

The accompanying drawing illustrates the invention.

DETAILED DESCRIPTION OF THE INVENTION

This invention is applicable to the purification of lower alkylene oxides having 2 to 4 carbon atoms such as propylene oxide prepared, for example, by reaction of an organic hydroperoxide with propylene and containing $C_4$-$C_8$ hydrocarbon contaminants, generally in amounts of 100 to 3000 ppm by weight, usually 200 to 1000 ppm.

As has been pointed out, in the preparation of $C_2$-$C_4$ alkylene oxides such as propylene oxide there are produced various impurities including $C_4$ to $C_8$ hydrocarbons as well as oxygen-containing materials such as water, low molecular weight alcohols, low molecular weight ketones, low molecular weight aldehydes and the like. In accordance with this invention, the impure alkylene oxide is subjected to extractive distillation with the glycol extractive solvent whereby hydrocarbon impurities are separated overhead as lights from the propylene oxide and solvent mixture. Thereafter, oxygenated impurities can be separated as by the procedure of U.S. Pat. No. 5,000,825.

The solvents used in the extractive distillation are glycols having 2 to 5 carbon atoms such as ethylene glycol, 1,2 propane diol, diethylene glycol, butane diol and pentane diol.

The method of this invention can be carried out either in a batch system or a continuous system. In the batch system the impure alkylene oxide, e.g., propylene oxide, is introduced into a vessel which can be heated and which is fitted with a fractionation column into which the extractive solvent can be introduced. The extractive solvent is introduced into the fractionating column at a point near the top of the column so that preferably there is some fractionation above the point of introduction. Reflux is also provided. The extractive solvent is suitably introduced at a temperature approximately the same as the boiling point of the mixture in the vessel at the point of introduction.

In the batch process the impure alkylene oxide mixture is heated to boiling and the solvent is introduced into the column in the appropriate amount. Hydrocarbon impurities are withdrawn overhead from the column with some alkylene oxide while the solvent and alkylene oxide, together with any contained oxygenated impurities, accumulate in the distillation vessel until finally all of the hydrocarbons or substantially all has been distilled overhead. A reflux to feed ratio of 0.2:1 to 5:1 generally is sufficient.

In the continuous system the feed consisting of the impure alkylene oxide mixture is introduced into a fractionation tower near the middle or lower section of the tower and the glycol extractive solvent is introduced into the upper section of the tower. The bottom of the tower is generally provided with a reboiler system to provide the necessary heat for fractionation. The bottoms from the tower consisting of the solvent and oxide as well as impurities such as methanol pass through the reboiler where it is heated by indirect exchange or by direct heat and a portion of the bottoms liquid thus heated and partially vaporized is recycled to the lower part of the column. The remaining portion is withdrawn. The overhead vapors comprised of the hydrocarbon impurities and some alkylene oxide are withdrawn from the tower and condensed. Usually in accordance with conventional practice a portion of the condensate is returned as recycle or reflux to the top of the tower. Reflux to feed ratios of about 0.2:1 to 5:1 are likewise appropriate. Such a system is well known in accordance with conventional engineering practices in extractive distillation processes and many modifications thereof are known and can be employed.

One embodiment of the foregoing description of the continuous system as it relates to propylene oxide purification is shown in the drawing wherein numeral 1 refers to the fractionation tower or extractive distillation zone which is provided with conventional trays, packing or the like. The impure propylene oxide mixture containing $C_4$ to $C_7$ hydrocarbon impurities is introduced into tower 1 through line 2, and the extractive solvent is introduced into tower 1 through line 3. The bottoms from the tower comprised of the propylene oxide substantially free of the hydrocarbon impurities and the solvent is removed through line 4 and passed through reboiler 5 wherein the bottoms are heated. Heated liquid is passed through line 6 and a portion is returned through line 7 to the tower 1 to provide the heat necessary for the distillation. The remaining portion of the bottoms is removed through line 8 and appropriately passed to a stripper (not shown) wherein purified propylene oxide is stripped overhead from a bottoms solvent stream which is recycled. The overhead vapors comprised of the hydrocarbon impurities and propylene oxide are withdrawn from the tower through line 9 and passed to condenser 10 and from condenser 10 through line 11 to receiver 12. A portion of the condensate can be returned to the top of the tower 1 through line 13, as reflux, and the remainder of the condensate is withdrawn from the receiver 12 through line 14.

The following examples are provided to illustrate the invention in greater detail and to demonstrate its utility. It will be understood, however, that the invention is not to be construed as being limited thereto.

EXAMPLE 1

A continuous extractive distillation run was carried out in an eighty-five (85) tray two-inch Oldershaw column with the solvent feed and propylene oxide feed at 25 and 40 trays from the top, respectively. The column was operated at 1 atmospheric pressure. About 392 grams/hr of propylene oxide containing 1000 ppm $C_4$-$C_7$ hydrocarbon impurities, mainly methyl pentanes and methyl pentenes, were fed to the distillation column at 40th tray from the top while monopropylene glycol solvent was fed to the 25th tray from the top at 257 grams/hr, a solvent to feed ratio of 0.66. The reflux to feed ratio was 2:1. About 633 grams/hr of propylene oxide and solvent were separated as bottoms while 16 grams/hr of hydrocarbon impurities together with propylene oxide were separated overhead. Overhead temperature was 34° C.; bottoms temperature was 50° C. The overhead was primarily propylene oxide and contained 2.4 wt. % hydrocarbon impurities. The propylene oxide and solvent bottoms stream was passed to a stripping column and a purified propylene oxide stream was recovered overhead. A bottoms propylene glycol solvent stream was separated and recycled. The purified propylene oxide contained 21 ppm hydrocarbon impurities.

EXAMPLE 2

A series of continuous extractive distillation runs was carried out in a fifty (50) tray one-inch Oldershaw column with the solvent feed and alkylene oxide (either propylene oxide or butylene oxide) feed at 15 and 25 trays from the top, respectively. The column was operated at one atmospheric pressure. Overhead temperature was between about 34° to 63° C.; bottoms temperature was between 50° to 95° C.

About 250 grams/hr. of alkylene oxide (propylene oxide or 1,2 butylene oxide) containing 1,000 to 1,100 ppm $C_4$ to $C_8$ hydrocarbon impurities were fed to the distillation column at the 25th tray from the top while the extractive solvent monopropylene glycol (1, 2 propanediol), monoethylene glycol, or butylene glycol (1, 4 butane diol) was fed to the 15th tray from the top at 150 grams/hr., a solvent to feed ratio of 0.6. Between 385 to 390 grams/hr. of alkylene oxide and solvent were separated as bottoms, and between 10 to 15 grams/hr. of hydrocarbon impurities together with alkylene oxide were separated overhead. The overhead stream was primarily alkylene oxide and contained between 1.6 and 3.0 wt. % hydrocarbon impurities.

The alkylene oxide and solvent bottoms stream was passed to a stripping column, and a purified alkylene oxide stream was recovered overhead.

The following Table 1 shows the comparative distillation results:

TABLE 1

| Run | Alkylene Oxide | Reflux/Feed Ratio | Solvent | PPM Hydrocarbon Impurities in Alkylene Oxide Bottom Product (Solvent Free Basis) |
|---|---|---|---|---|
| 16 | Propylene Oxide | 2.1 | — | 990 |
| 16a | Propylene Oxide | 2.0 | MPG* | 45 |
| 16b | Propylene Oxide | 2.1 | MEG** | 52 |
| 16d | Propylene Oxide | 1.9 | MBG*** | 120 |
| 18 | Butylene Oxide | 2.1 | — | 860 |
| 18b | Butylene Oxide | 2.0 | MPG* | 80 |
| 18c | Butylene Oxide | 1.8 | MEG** | 98 |
| 18e | Butylene Oxide | 2.2 | MBG*** | 156 |

*1,2 propanediol
**ethylene glycol
***1,4 butanediol

These results demonstrate that when no extractive solvent was used (Runs 16 and 18), the majority of hydrocarbon impurities remained in the alkylene oxide stream. Only 10 to 22% of hydrocarbon impurities in the feed were removed.

When the glycol solvent was used, however, between 86 and 96% of hydrocarbon impurities were removed from alkylene oxide.

A very high purity of alkylene oxide was produced in accordance with the invention, i.e., alkylene oxide containing less than 160 ppm hydrocarbon.

What is claimed is:

1. An extractive distillation process for the separation of hydrocarbon impurities having 4 to 7 carbon atoms from propylene oxide which consists essentially of introducing a feed comprised of propylene oxide containing said hydrocarbon impurities in amount of 100 to 3000 ppm into an intermediate section of an extractive distillation zone, introducing C2-C5 glycol extractive distillation solvent into the upper section of said extractive distillation zone, distilling said hydrocarbon impurities overhead from said extractive distillation zone and removing a mixture comprised of said glycol solvent and said propylene oxide substantially free of said hydrocarbon impurities from the lower section of the said extractive distillation zone.

2. The method of claim 1 wherein said extractive distillation solvent is monopropylene glycol.

3. The method of claim 1 wherein said extractive distillation solvent is monoethylene glycol.

4. The method of claim 1 wherein said extractive distillation solvent is 1,4 butanediol.

* * * * *